United States Patent [19]

Schickaneder et al.

[11] Patent Number: 4,833,141
[45] Date of Patent: May 23, 1989

[54] 4-[4-[[2-(HALOPHENYL)-2-[1H-TR:AZOL(OR DIAZOL)-1-YLMETHYL)-1,3-DIOXOLAN-4-YL]METHOXY]PHENYL]-PIPERAZINE-1-CARBIMIC ACIDS HAVING ANTIMYCOTIC ACTIVITY

[75] Inventors: Helmut Schickaneder, Eckental; Rolf Herter, Schwabach; Hartmut Vergin, Nuremberg; Heidrun Engler, Cadolzburg; Kurt H. Ahrens, Nuremberg, all of Fed. Rep. of Germany

[73] Assignee: Heumann Pharma GmbH & Co., Nuremberg, Fed. Rep. of Germany

[21] Appl. No.: 69,159

[22] Filed: Jul. 2, 1987

[30] Foreign Application Priority Data

Jul. 7, 1986 [DE] Fed. Rep. of Germany ....... 3622791

[51] Int. Cl.[4] .................. A61K 31/41; A61K 31/335; A61K 31/415; A61K 31/425
[52] U.S. Cl. ................... 514/252; 544/366; 544/367; 544/370
[58] Field of Search ............ 544/367, 366, 30; 514/252

[56] References Cited

U.S. PATENT DOCUMENTS 3,790,594  2/1974  Meiser et al. .......................... 544/60
4,144,346  3/1979  Heeres et al. ......................... 546/210
4,335,125  6/1982  Heeres et al. ......................... 544/370
4,391,805  7/1983  Blume et al. ......................... 544/370

FOREIGN PATENT DOCUMENTS 0006722  1/1980  European Pat. Off. .
0007696  2/1980  European Pat. Off. .
0152596  8/1985  European Pat. Off. .

Primary Examiner—Donald G. Daus
Assistant Examiner—C. Shen
Attorney, Agent, or Firm—Burns, Doane, Swecker & Mathis

[57] ABSTRACT

The invention relates to new 1,4-piperazine compounds corresponding to the following general formula

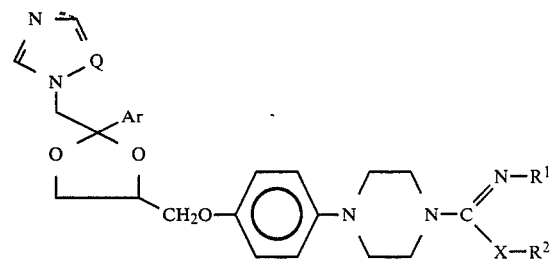

which show improved antimycotic activity in relation to the known compounds miconazol and ketoconazol.

6 Claims, No Drawings

4-[4-[[2-(HALOPHENYL)-2-[1H-TR:AZOL(OR DIAZOL)-1-YLMETHYL]-1,3-DIOXOLAN-4-YL]METHOXY]PHENYL]-PIPERAZINE-1-CARBIMIC ACIDS HAVING ANTIMYCOTIC ACTIVITY

This invention relates to new compounds showing antimycotic activity.

Several antimycotically active compounds, including e.g. miconazol (DE-AS No. 19 40 388) or ketoconazol (DE-OS No. 28 04 096), are already known.

The object of the present invention is to provide new compounds showing improved antimycotic activity. This object is achieved by the invention.

The present invention relates to new 1,4-piperazine compounds corresponding to the following general formula

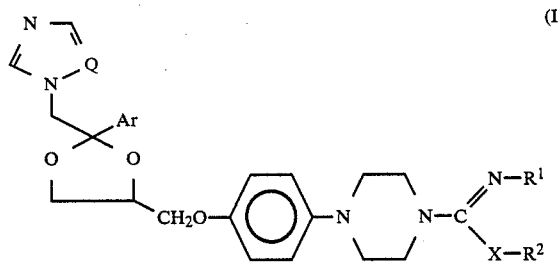

in which
Q represents CH or N,
Ar is an unsubstituted phenyl group or a phenyl group substituted by up to 2 halogen atoms,
X is an oxygen or sulfur atom,
$R^1$ is a hydrogen atom or a lower alkyl radical and
$R^2$ is a $C_1$–$C_{10}$ alkyl, cycloalkyl, $C_1$–$C_{10}$ alkenyl, halogen-$C_1$–$C_{10}$ alkyl, hydroxy-$C_1$–$C_{10}$ alkyl, $C_1$–$C_{10}$-alkoxy-$C_1$–$C_{10}$-alkyl, di-$C_1$–$C_{10}$-alkylamino-$C_1$–$C_{10}$-alkyl, Ar lower alkyl or aryl radical which is either unsubstituted or substituted by 1 to 3 substituents from the group comprising halogen atoms, lower alkyl and lower alkoxy groups, and to physiologically acceptable hydrates and salts thereof.

In general formula I, Q represents CH or N, preferably N.

Ar is an unsubstituted phenyl group or a phenyl group substituted by up to 2 halogen atoms, the monosubstitution of the phenyl group being preferred. The halogen substituents in question are fluorine, chlorine and bromine atoms, preferably fluorine and chlorine atoms. In the case of the monosubstitution, the halogen atom is preferably arranged in the 4-position of the phenyl ring. In the case of the disubstitution, the substituents are preferably arranged in the 2- and 4-position of the phenyl ring.

In general formula I, X is an oxygen or sulfur atom, preferably an oxygen atom.

$R^1$ is a hydrogen atom or a lower alkyl radical. By "lower alkyl" is meant a radical containing from 1 to 4 carbon atoms. Examples of lower alkyl radicals are the methyl, ethyl, n-propyl, i-propyl, n-butyl, i-butyl, sec.-butyl and tert.-butyl group. Groups containing from 1 to 3 carbon atoms are preferred.

In general formula I, the substituent $R^2$ is a $C_1$–$C_{10}$ alkyl group, preferably a $C_1$–$C_5$ alkyl group and, more preferably, a lower alkyl group as defined above. Preferred examples of such groups are methyl, ethyl, propyl, butyl, isopropyl and isobutyl. Further, the substituent $R^2$ in general formula I represents a $C_5$–$C_{12}$ cycloalkyl group, rings containing from 5 to 9 and 12 carbon atoms being preferred. Preferred individual examples are cyclopentyl, cyclohexyl, cycloheptyl, cyclo-octyl and cyclododecyl. The substituent $R^2$ may also be a $C_1$–$C_{10}$ alkenyl group, preferably a $C_1$–$C_5$ alkenyl group and, more preferably, a lower alkenyl group as defined above. Preferred individual examples are allyl and crotyl. The substituent $R^2$ may also be a halogen-$C_1$–$C_{10}$ alkyl group, preferably a halogen-$C_1$–$C_5$-alkyl group and more preferably a halogen lower alkyl group as defined above. The halogen atoms in question are fluorine, chlorine and bromine atoms. The $C_1$–$C_{10}$ alkyl group may be substituted by 1 to 3 halogen atoms which may be attached to the same carbon atom or to different carbon atoms. The $C_1$–$C_{10}$ alkyl group is preferably substituted by 1 to 3 chlorine or fluorine atoms. Preferred individual examples are 2-fluoroethyl, 2,2,2-trifluoroethyl, 2-chloropropyl and 4-chlorobutyl. $R^2$ may also be a hydroxy-$C_1$–$C_{10}$-alkyl group, preferably a hydroxy-$C_1$–$C_5$alkyl group and more preferably a hydroxy lower alkyl group as defined above. One preferred example is hydroxyethyl. $R^2$ may also be a $C_1$–$C_{10}$ alkoxy-$C_1$–$C_{10}$-alkyl group, preferably a $C_1$–$C_5$-alkoxy-$C_1$–$C_5$-alkyl group and more preferably a lower alkoxy lower alkyl group as defined above. A preferred example is methoxyethyl. $R^2$ may also be a di-$C_1$–$C_{10}$-alkylamino-$C_1$–$C_{10}$alkyl group, preferably a di-$C_1$–$C_5$-alkylamino-$C_1$–$C_5$-alkyl group and more preferably a di-lower alkylamino lower alkyl group. The nitrogen atom of the di-$C_1$–$C_{10}$-alkylamino group may be substituted by the same or different $C_1$–$C_{10}$-alkyl groups. A preferred example of such a group is dimethyl aminoethyl. Finally, $R^2$ may also be an aralkyl group, preferably the benzyl group. The aralkyl group may either be unsubstituted or substituted by 1 to 3 substituents from the group comprising halogen atoms as defined above, lower alkyl groups as defined above and lower alkoxy groups as defined above. Preferred substituents of the aralkyl group are lower alkyl groups, such as in particular methyl and ethyl; halogen atoms, such as fluorine and chlorine, and alkoxy groups, such as methoxy.

A preferred group of the compounds according to the invention is characterized in that X is an oxygen atom and $R^1$ is a hydrogen atom, the substituents Q, Ar and $R^2$ having the meanings defined above.

The compounds of general formula I according to the invention may be prepared as follows:

(a) Compounds corresponding to general formula I, in which $R^1$ is hydrogen and $R^2$, Q, Ar and X are as defined above, may be prepared ($a_1$) by reaction of a compound corresponding to general formula II

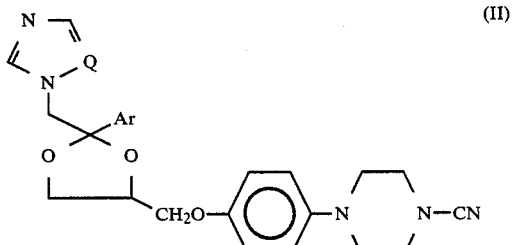

in which Q and Ar are as defined above, with a compound corresponding to the following general formula

  (III)

in which $R^2$ and X are as defined above.

The reaction is carried out in the usual way in the presence of mineral acids, such as hydrochloric acid for example, and by addition of an inert solvent, such as for example a chlorinated hydrocarbon, for example chloroform.

However, the reaction is preferably carried out in a basic medium. The solvent used is a compound corresponding to the following general formula

in which $R^2$ is as defined above, or a mixture of the compound $R^2XH$ and an inert solvent, for example an ether, such as THF, a hydrocarbon, such as toluene, or a chlorinated hydrocarbon, such as dichloroethane. The compound $R^2XH$ is preferably used in at least the stoichiometric quantity. The base used may be the sodium salt of the compound $R^2XH$ or an alkali or alkaline earth hydroxide or cyanide. The base is used in a quantitative ratio of from 0.01 to 3 mole equivalents and preferably 0.1 mole equivalent, based on compound II. The reaction temperature may be varied between 20° C. and the reflux temperature of the particular medium used.

The compound of general formula II used as starting compound in the above reaction may be obtained, for example, by reaction of a compound corresponding to the following general formula

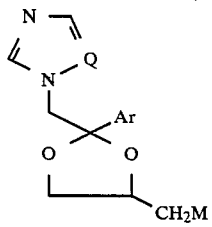 (IX)

in which Q and Ar are as defined above and M is the ester of methane sulfonic acid or toluene sulfonic acid, with a compound corresponding to the following general formula

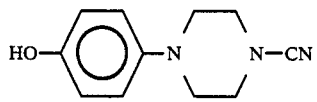 (XII)

The reaction is carried out in the usual way using a base, such as sodium hydride or carbonate, in an inert solvent, such as DMF, and at elevated temperature, preferably at 60° to 120° C.

Alternatively, the starting compound II may also be obtained by reaction of a compound corresponding to the following general formula

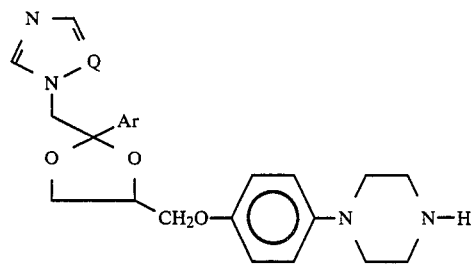 (IV)

in which Q and Ar are as defined above, with cyanogen chloride or cyanogen bromide. The reaction is preferably carried out in an inert solvent, such as dichloromethane, tetrahydrofuran, etc. The base used is a tertiary amine, preferably triethylamine, or an inorganic base, such as calcium hydroxide or potassium carbonate.

Another possible method of synthesizing the compound corresponding to general formula II comprises reacting a compound corresponding to the following general formula

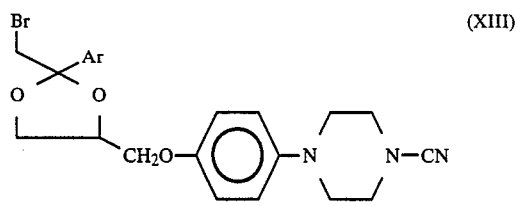 (XIII)

in which Ar is as defined above, with a compound corresponding to the following general formula

 (XIV)

in which Q is as defined above.

The reaction may be carried out, for example, in dimethylformamide or dimethyl sulfoxide at a temperature of from 60° to 180° C. and preferably at a temperature of from 130° to 150° C. The base used is, in particular, sodium hydride or an inorganic base, such as potassium carbonate.

The compound of general formula XIII used in this synthesis may be obtained, for example, by reaction of a compound corresponding to the following general formula

 (XV)

in which Ar is as defined above and M is the ester of methane sulfonic acid or toluene sulfonic acid, with a compound corresponding to the following general formula

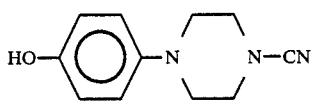   (XII)

The reaction may be carried out under the same conditions as described above for the reaction of the compound of general formula IX with the compound of formula XII. or (a₂) by reaction of a compound corresponding to general formula IV

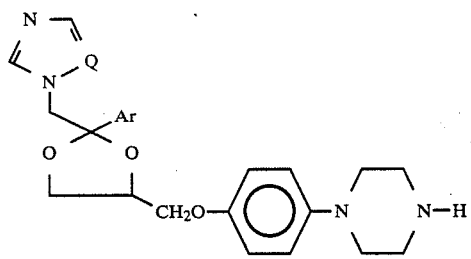   (IV)

in which Q and Ar are as defined above, with a compound corresponding to the following general formula

R²XCN   (V)

in which R² and X are as defined above.

The starting compound of general formula VI, which may readily be obtained by methods known from the literature, is reacted in an equimolar quantity with the compound corresponding to general formula IV in an inert solvent. Suitable solvents are ethers, such as tetrahydrofuran, hydrocarbons, such as toluene, and chlorinated hydrocarbons, such as dichloroethane. The reaction may be carried out at temperatures of from −20° C. to +40° C. and preferably at temperatures of from 0° to 10° C. The reaction mixture is worked up by concentration and crystallization of the residue.

(b) Compounds corresponding to general formula I, in which R¹ represents hydrogen, R² is as defined above, but with the proviso that R² is not an aryl radical, X is a sulfur atom and Q and Ar are as defined above, may be prepared by reaction of a compound corresponding to the following general formula

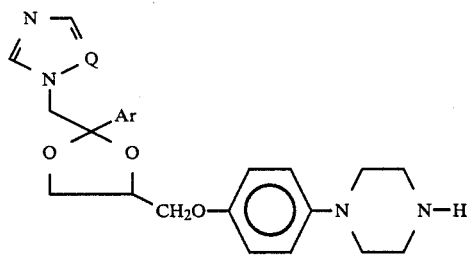   (IV)

in which Q and Ar are as defined above, with a compound corresponding to the following general formula

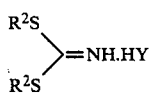   (VI)

in which R² is as defined above and HY is an inorganic acid. The inorganic acid HY may be, for example, HCl, HBr, HI or (H₂SO₄)₁/₂.

The reaction may be carried out in an inert solvent, for example an ether, such as tetrahydrofuran, a chlorinated hydrocarbon, such as dichloroethane, or preferably a nitrile, more especially acetonitrile. A reaction temperature of from 60° to 100° C. is preferred. The reaction mixture is worked up either by concentration, in which case the product accumulates as a salt of the acid HY, or by prior removal of the acid HY with an aqueous-alkaline solution and concentration of the organic phase, in which case the product is obtained as free base.

(c) Compounds corresponding to general formula I, in which R¹, R², Q and Ar are as defined above and X is a sulfur atom, may be obtained by reaction of a compound corresponding to the following general formula

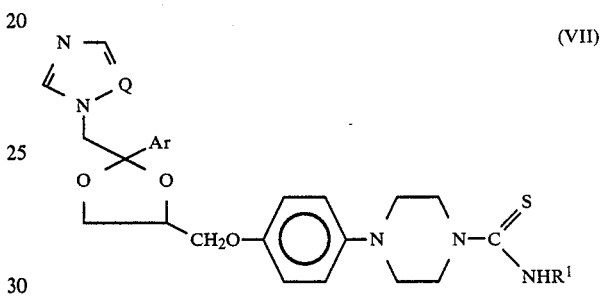   (VII)

in which Q, Ar and R¹ are as defined above, with a compound corresponding to the following general formula

R²Z   (VIII)

in which R² is as defined above and Z is a leaving group. Where R² in the compound corresponding to formula VIII is an aliphatic group, Z may be, for example, halogen, such as chlorine, bromine and iodine, methane sulfonate, benzenesulfonate or toluene sulfonate.

The reaction is carried out at 0° to 150° C. in an inert solvent which may be, for example, an ether, such as tetrahydrofuran, a hydrocarbon, such as toluene, a chlorinated hydrocarbon, such as chloroform or 1,2-dichloroethane, or a nitrile, such as acetonitrile. A tertiary amine or an inorganic basic salt, such as calcium hydroxide or calcium carbonate, may be added as base. If no base is added during the reaction, the reaction mixture is worked up in the presence of an aqueous alkaline solution.

However, if the substituent R² in the compound corresponding to general formula VIII is an aryl group, Z must be a diazonium group. In this case, the reaction is preferably carried out in a two-phase system of water and a chlorinated hydrocarbon, the chlorinated hydrocarbon preferably being 1,2-dichloroethane. In this case, 0.01 to 0.1 mole equivalent of a phase transfer catalyst, such as (n-Bu)₄NHSO₄, is added to the reaction mixture. The reaction temperature is in the range from 10° C. to the reflux temperature of the organic solvent used. The reaction product is worked up and isolated in the usual way.

The compound corresponding to general formula VII used as starting compound in this variant may be obtained in known manner from a compound corresponding to the following general formula

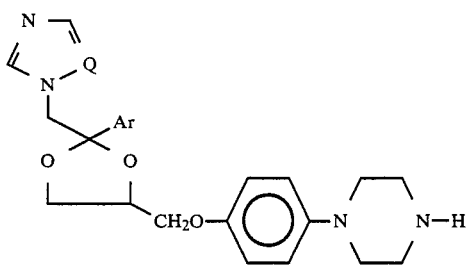
(IV)

in which Q and Ar are as defined above, and an isothiocyanate corresponding to the following general formula $R^1NCS$ (XVI)

in which $R^1$ is as defined above.

(d) Compounds corresponding to general formula I, in which $R^1$ is a hydrogen atom, X is an oxygen atom and $R^2$, Q and Ar are as defined above, may be obtained by reaction of a compound corresponding to the following general formula

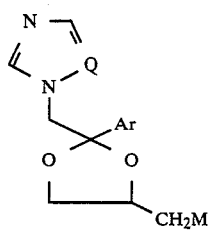
(IX)

in which Q and Ar are as defined above and M is the ester of methane sulfonic acid or toluene sulfonic acid, with a compound corresponding to the following general formula

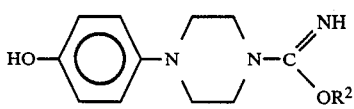
(X)

in which $R^2$ is as defined above. The reactive ester group used is, for example, a methane sulfonate, benzene-sulfonate or 4-toluene sulfonate group. The reaction may be carried out under the same conditions as described above for the reaction of the compound corresponding to general formula IX with the compound corresponding to general formula XII.

The compound of general formula X used as starting compound in this variant may in turn readily be obtained from the compound

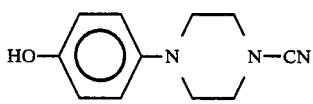
(XII)

and the compound corresponding to general formula III $R^2XH$ (III)

The reaction may be carried out under the same conditions as described above for variant ($a_1$).

(e) Compounds corresponding to general formula I, in which $R^1$ is a lower alkyl radical, X is an oxygen atom and $R^2$, Q and Ar are as defined above, may be obtained by reaction of a compound corresponding to the following general formula

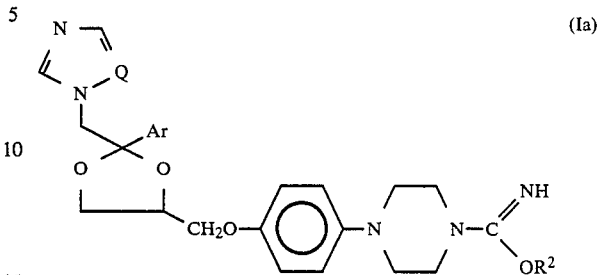
(Ia)

in which Q, Ar and $R^2$ are as defined above, with a compound corresponding to the following general formula $R^1Z$ (XI)

in which $R^1$ is a lower alkyl radical as defined above and Z is a leaving group. The leaving group Z may be, for example, a halogen atom, such as chlorine, bromine and iodine, or a methane sulfonate, benzenesulfonate or toluene sulfonate group. The reaction is carried out in an inert solvent, for example an ether, such as tetrahydrofuran, a hydrocarbon, such as toluene, a halogenated hydrocarbon, such as dichloroethane, a nitrile, such as acetonitrile, or an amide, such as dimethylformamide. The reaction temperature is in the range from 20° C. to the reflux temperature of the solvent. At least a stoichiometric quantity of a base is preferably added to the reaction mixture, the base being either a tertiary amine or an inorganic base, such as sodium hydride or potassium carbonate.

The compounds obtained by variants (a) to (e) above are isolated and purified in the usual way, for example by chromatographic methods, recrystallization, extraction, etc.

As mentioned above, the compounds obtained in steps (a) to (e) may be converted into their physiologically acceptable salts with suitable acids of the type described above.

The compounds according to the invention show both considerably improved in vitro antimycotic activity and also better therapeutically useful in vivo activity than, for example, miconazol or ketoconazol.

The new compounds are suitable for the external and oral treatment of fungal infections in human beings and animals.

The new compounds may be formulated, for example, as tablets, capsules, suspensions, solutions, gels, creams, ointments, etc.

The therapeutically active compound is present in pharmaceutical preparations preferably in a concentration of from 0.01 to 90% by weight, based on the mixture as a whole.

The in-use concentration for solutions, gels, creams or ointments is generally from 0.1 to 4% by weight.

For oral administration in the form of tablets or capsules, the daily dose of the active principle is from about 1.0 to 50.0 mg/kg bodyweight in admixture with a standard excipient.

The preparation of the compounds according to the invention and their starting products are described in the following Examples.

EXAMPLE 1

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-[2-(N,N-dimethylamino)-ethyl]-ester

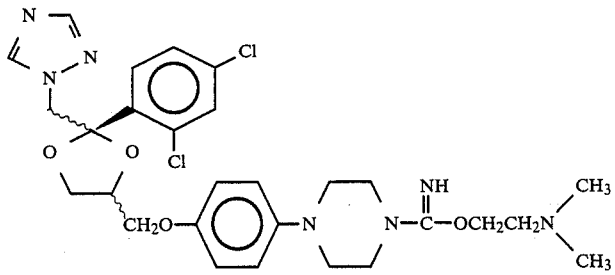

1.80 g (3.5 mmoles) (±)-cis-1-cyano-4-[4-[[2-(2,4-dichlorophenyl)-2-(1H-1,2,4-triazol-1-ylmethyl)-1,3-dioxolan-4-yl]-methoxy]-phenyl]-piperazine are heated under reflux in a solution of 8 mg (0.35 mmole) sodium in 10 ml N,N-dimethylaminoethanol and 20 ml toluene. After 2 h, the reaction product is concentrated in vacuo and, after the addition of 20 ml $H_2O$, is extracted three times with 25 ml ethyl acetate each. The solvent is distilled off in vacuo, leaving 2.5 g of an oil. This oil is dissolved in a little ethyl acetate. After cooling in an ice bath, the title compound precipitated is isolated by filtration under suction.

Yield: 1.45 g (69% of the theoretical)
Cream-colored crystals melting at 102°–104° C.
Rf: 0.26 (silica gel; dichloromethane/methanol/$NH_3$(25%) 90/9/1)
$C_{28}H_{35}Cl_2N_7O_4$ (M: 604.5)
Calculated: C, 55.63; H, 5.84; N, 16.22, Found: C, 55.96; H, 5.80; N, 16.09.

| $^1$H—NMR-data: (CDCl$_3$, TMS as internal standard) | δ = 2.32 (s) 6 H, 2.67 (t) 2 H, 3.08 (m) 4 H, 3.51 (m) 5 H, 3.87 (m) 3 H, 4.19 (t) 2 H, 4.38 (m) 1 H, 4.4–5.1 (broad) 1 H, exchangeable with D$_2$O 4.82 (s) 2 H, 6.88 (m) 4 H, 7.2–7.8 (m) 3 H, 7.93 1 H, 8.26 1 H ppm. |
|---|---|

Preparation of
(±)-cis-1-cyano-4-[4-[[2-(2-4,dichlorophenyl)-2-(1H-1,2,4-triazol-1-ylmethyl)-1,3-dioxolan-4-yl]-methoxy]-phenyl]-piperazine

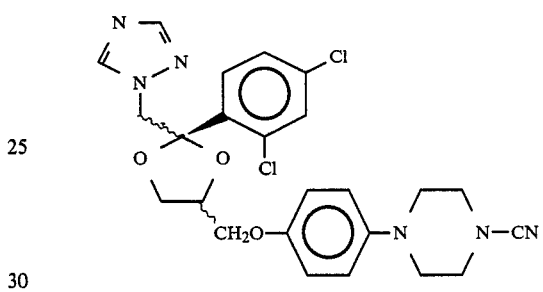

METHOD A 4.45 g (42 mmoles) cyanogen bromide in 70 ml dichloromethane are added dropwise while cooling with ice to a solution of 19.62 g (40 mmoles) of (±)-cis-1-[4-[[2-(2,4-dichlorophenyl)-2-(1H-1,2,4-triazol-1-ylmethyl)-1,3-dioxolan-4-yl]-methoxy]-phenyl]-piperazine and 4.25 g (42 mmoles) triethylamine in 70 ml dichloromethane. After stirring for 12 h at room temperature, the reaction mixture is poured onto 16 g $K_2CO_3$ in 150 ml $H_2O$ and extracted with dichloromethane.

Removal of the solvent by distillation in vacuo leaves an oil which is crystallized by treatment with ethyl acetate. The primary crystallizate is recrystallized from a little methanol.

Yield: 15.4 g (=74% of the theoretical)
Colorless powder melting at 135° C.
Rf=0.41 (ethylacetate/methanol 95/5)
$C_{24}H_{24}Cl_2N_6O_3$ (M: 514.4)
Calculated: C, 55.93; H, 4.69; N, 16.31; Found: C, 56.04; H, 4.71; N, 16.29.

| $^1$H—NMR-data: (CDCl$_3$, TMS as internal standard) | δ = 3.13 (m) 4 H, 3.37 (m) 4 H, 3.45–4.1 (m) 4 H, 4.38 (m) 1 H, 4.83 (s) 2 H, 6.92 (m) 4 H, 7.2–7.75 (m) 3 H, 7.93 (s) 1 H, 8.28 (s) 1 H ppm. |
|---|---|

METHOD B

A solution of 996 mg (4.9 mmoles) 1-cyano-4-(4-hydroxy-phenyl)-piperazine in 10 ml DMF is added dropwise to 177 mg (5.9 mmoles) sodium hydride (80% dispersion in mineral oil) likewise in 10 ml DMF. 2.30 g (4.9 mmoles) (±)-cis-[2-(2,4-dichlorophenyl)-2-(1H-1,2,4-triazol-1-ylmethyl)-1,3-dioxolan-4-yl]-methyl-4-toluene sulfonate in 12 ml DMF are then added, followed by heating for 45 minutes to 90° C. The reaction mixture is concentrated in vacuo and the organic phase is washed with H$_2$O and dried over MgSO$_4$. Removal of the solvent leaves a reddish oil which crystallizes from ethyl acetate. Recrystallization from methanol gives the title compound in the form of a white powder. Yield: 1.2 g (=48% of the theoretical)

METHOD C (±)-cis-[2-(bromomethyl)-2-(2,4-dichlorophenyl)-1,3-dioxolan-4-ylmethyl]-4-toluene sulfonate

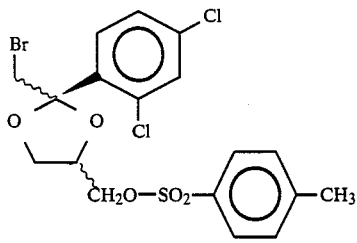

A solution of 60.3 g (310 mmoles) 4-toluene sulfonic acid chloride in 300 ml dichloromethane is added dropwise to a solution of 102.4 g (299 mmoles) (±)-cis-2-(bromomethyl)-2-(2,4-dichlorophenyl)-1,3-dioxolane-4-methanol in 400 ml dichloromethane and 73 ml pyridine. After stirring for 12 h at room temperature, the reaction mixture is washed successively with water, dilute aqueous HCl and aqueous NaHCO$_3$ solution and the organic phase is dried over magnesium sulfate. Removal of the solvent in vacuo leaves a light yellow oil which is pure enough for further reactions. Yield 132.0 g (89% of the theoretical)

Rf: 0.70 (silica gel; ethyl acetate/petroleum ether 60/40). (±)-cis-1-[4-[[2-(bromomethyl)-2-(2,4-dichlorophenyl)-1,3-dioxolan-4-yl]-methoxy]-phenyl]-4-cyanopiperazine

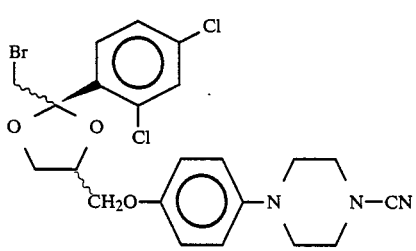

A solution of 4.07 g (20 mmoles) 1-cyano-4-(4-hydroxy-phenyl)-piperazine and a solution of 9.92 g (20 mmoles) of the compound obtained as described above are successively added dropwise to 675 mg (22.5 mmoles) NaH (80% dispersion in mineral oil) in 20 ml DMF. The reaction mixture is heated at 80°–90° C. for 20 h. It is then poured onto water and extracted with dichloromethane. The organic phase is concentrated in vacuo and the residue chromatographed on silica gel (ethyl acetate/petroleum ether 50°–70° C., 60/40).

Yield: 3.6 g (34% of the theoretical)
Colorless solid melting at 138.5° to 139.5° C.
Rf: 0.59 (silica gel; ethyl acetate/petroleum ether 60/40)
C$_{22}$H$_{22}$BrCl$_2$N$_3$O$_3$ (M: 527.3)

| $^1$H—NMR data: (CDCl$_3$, TMS as internal standard) | δ = 3.12 (m) 4 H, 3.37 (m) 4 H, 3.65–4.6 (m) 7 H, 6.92 (s) 4 H, 7.15–7.8 (m) 3 H ppm. |
|---|---|

(±)-cis-1-cyano-4-[4-[[2-(2,4-dichlorophenyl)-2-(1H-1,2,4-triazol-1-ylmethyl)-1,3-dioxolan-4-yl]-methoxy]-phenyl]-piperazine A solution of 0.8 g (11.4 mmoles) 1,2,4-triazole is added dropwise at room temperature to 340 mg (11.4 mmoles) sodium hydride (80% dispersion in mineral oil) in 10 ml DMF. After the evolution of hydrogen has stopped, 1.5 g (2.9 mmoles) of the compound obtained as described above are added. After heating for 12 h at 140° C., the reaction mixture is poured onto water and extracted with dichloroethane. Removal of the solvent by distillation in vacuo leaves a dark brown, viscous oil. The title compound crystallizes in the form of a pale beige-colored solid by addition of a little methanol.

The spectroscopic and chromatographic data accord with those reported further above.

EXAMPLE 2

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(2-propenyl)-ester

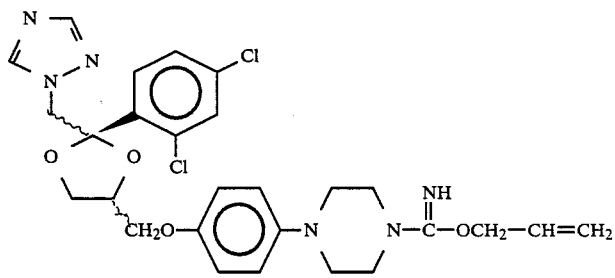

This compound is prepared in the same way as in Example 1, but with 2-propanol.

Colorless crystals melting at 105° to 107° C.
Rf: 0.52 (silica gel; ethyl acetate/methanol/triethylamine 85/10/5)
C$_{27}$H$_{30}$Cl$_2$N$_6$O$_4$ (M: 573.5)

| $^1$H—NMR data: (CDCl$_3$, TMS as internal standard) | δ = 3.10 (m) 4 H, 3.53 (m) 5 H, 3.89 (m) 3 H, 4.38 (m) 1 H, 4.63 (d) 2 H, 4.83 (s) 2 H, |
|---|---|

-continued

| | 4.2–5.1 (broad), 1 H, exchangeable with D₂O, 5.1–5.6 (m) 2 H, 5.7–6.4 (m) 1 H, 6.93 (m) 4 H, 7.2–7.75 (m) 3 H, 7.94 (s) 1 H, 8.27 (s) 1 H ppm. |
|---|---|

EXAMPLE 3

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid ethyl ester This compound is prepared as in Example 1, but with ethanol.

Cream-colored powder melting at 102°–103° C.

Rf: 0.33 (silica gel; ethyl acetate/methanol/triethylamine 85/10/5)

$C_{26}H_{30}Cl_2N_6O_4$ (M: 561.5)

| ¹H—NMR data: (CDCl₃, TMS as internal standard) | δ = 1.32 (t) 3 H, 3.07 (m) 4 H, 3.5 (m) 5 H, 3.88 (m) 3 H, 4.11 (q) 2 H, 4.33 (m) 1 H, 4.24 (broad s) 1 H, exchangeable with D₂O, 4.83 (s) 2 H, 6.88 (m) 4 H, 7.2–7.75 (m) 3 H, 7.94 (s) 1 H, 8.26 (s) 1 H ppm. |
|---|---|

EXAMPLE 4

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid benzylester This compound is prepared as in Example 1, but with benzylalcohol.

Colorless crystals melting at 101°–103° C.

Rf: 0.37 (silica gel; ethyl acetate/methanol/triethylamine 90/5/5)

$C_{31}H_{32}Cl_2N_6O_4$ (M: 623.5)

| ¹H—NMR data: (CDCl₃, TMS as internal standard) | δ = 3.1 (m) 4 H, 3.55 (m) 5 H, 3.9 (m) 2 H, 4.21 (broad s) 1 H, exchangeable with D₂O, 4.4 (m) 1 H, 4.83 (s) 2 H, 5.19 (s) 2 H, 6.90 (m) 4 H, 7.25–7.75 (m) 3 H, 7.44 (s) 5 H, 7.95 (s) 1 H, 8.27 (s) 1 H ppm. |
|---|---|

EXAMPLE 5

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-cyclohexyl ester This compound is prepared as in Example 1, but with cyclohexanol.

Colorless crystals melting at 99°–101° C.

Rf: 0.40 (silica gel, ethyl acetate/methanol/triethylamine 90/5/5)

$C_{30}H_{35}Cl_2N_6O_4$ (M: 614.6)

| ¹H—NMR data: (CDCl₃, TMS as internal standard) | δ = 1.15–2.25 (m) 10 H, 3.08 (m) 4 H, 3.5 (m) 5 H, 3.88 (m) 4 H, 1 H exchangeable with D₂O, 4.38 (m) 1 H, 4.63 (m) 1 H, 4.82 (s) 2 H, 6.88 (m) 4 H, 7.2–7.8 (m) 3 H, 7.94 (s) 1 H, 8.29 (s) 1 H ppm. |
|---|---|

EXAMPLE 6

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-butylester

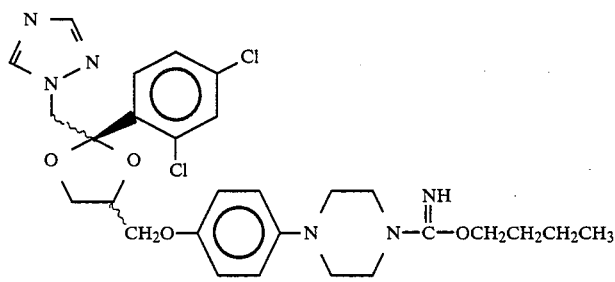

This compound is prepared as in Example 1, but with 1-butanol.

Pale yellow-colored crystals melting at 89°–92° C.

Rf: 0.38 (silica gel; ethyl acetate/methanol/triethylamine 85/10/5)

$C_{28}H_{34}Cl_2N_6O_4$ (M: 589.5)

| $^1$H—NMR data: (CDCl$_3$, TMS as internal standard) | δ = 0.93 (m) 3 H, 1.1–1.9 (m) 4 H, 3.07 (m) 4 H, 3.50 (m) 5 H, 3.85 (m) 3 H, 4.03 (t) 2 H, 4.33 (m) 2 H, 1 H exchangeable with D$_2$O, 4.80 (s) 2 H, 6.85 (m) 4 H, 7.2–7.75 (m) 3 H, 7.92 (s) 1 H, 8.24 (s) 1 H ppm. |
|---|---|

EXAMPLE 7

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-thiocarbimic acid-butylester

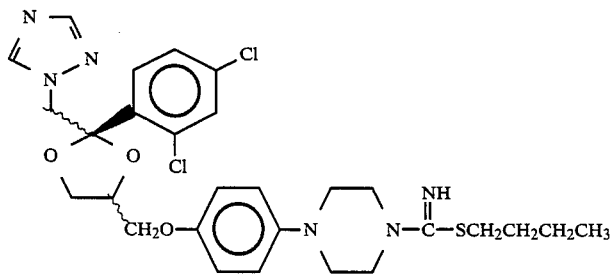

This compound is prepared as in Example 1, but with 1-butanethiol.

Beige-colored crystalline solid melting at 122°–124° C.

Rf: 0.47 (silica gel; ethyl acetate/methanol/triethylamine 90/5/5)

$C_{28}H_{34}Cl_2N_6O_3S$ (M: 605.6)

| $^1$H—NMR data: (TMS as internal standard) | δ = 0.94 (m) 3 H, 1.1–1.9 (m) 4 H, 2.81 (t) 2 H, 3.12 (m) 4 H, 3.4–4.2 (m) 8 H, 4.38 (m) 1 H, 4.5–5.2 (broad) 1 H, exchangeable with D$_2$O, 4.82 (s) 2 H, 6.87 (m) 4 H, 7.2–7.8 (m) 3 H, 7.93 (s) 1 H, 8.26 (s) 1 H ppm. |
|---|---|

EXAMPLE 8

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-methylester fumarate

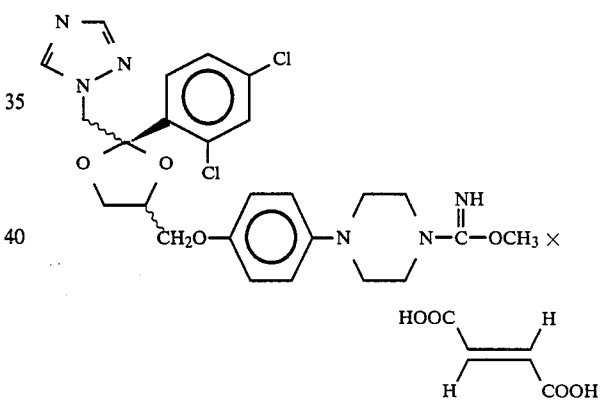

25.0 g (48.5 mmoles) (±)-cis-1-cyano-4-[4-[[2-(2,4-dichlorophenyl)-2-(1H-1,2,4-triazol-1-ylmethyl)-1,3-dioxolan-4-yl]-methoxy]-phenyl]-piperazine are heated under reflux in a solution of 112 mg (4.9 mmoles) sodium in 65 ml methanol and 125 ml toluene. After 4 h, the reaction mixture is concentrated in vacuo, taken up in 200 ml CH$_3$OH/CH$_2$Cl$_2$ (20/80 V/V) and washed with a little water. The solvent is distilled off in vacuo and 16.05 g of an oil are obtained.

The oil is dissolved with heating in 200 ml acetone, followed by the addition of a solution of 3.57 g (30.8 mmoles) fumaric acid in 50 ml EtOH. After cooling to room temperature, the fumarate precipitated is isolated by filtration under suction and washed with a little acetone.

Yield: 15.1 g (=47% of the theoretical)

Colorless solid melting at 160°–163° C. (differential thermal analysis).

Rf=0.32 (ethyl acetate/methanol/triethylamine 85/10/5)

$C_{29}H_{32}Cl_2N_6O_8$ (M: 663.5)

Calculated: C, 52.49; H, 4.82; N, 12.67; Found: C, 52.19; H, 4.81; N, 12.39.

| $^1$H—NMR data: (d$_6$-DMSO, TMS as internal standard) | δ = 3.12 (m) 4 H, 3.3–4.15 (m) 8 H, 3.99 (s) 3 H, 4.39 (t) 1 H, 4.86 (s) 2 H, 6.63 (s) 2 H, 6.96 (s) 4 H, 7.35–7.80 (m) 3 H, 7.93 (s) 1 H, 8.48 (s) 1 H, 10.33 (s) 3 H (exchangeable with D$_2$O) ppm. |
|---|---|

EXAMPLE 9

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-isopropylester fumarate

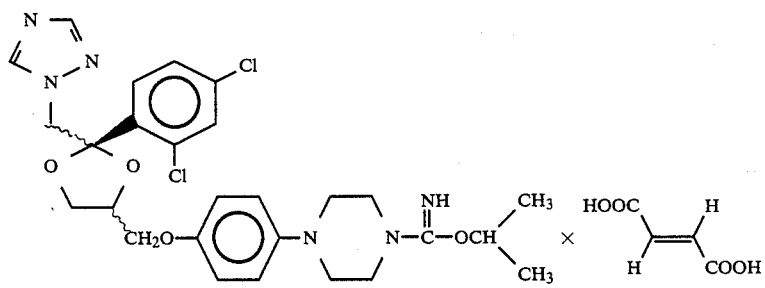

This compound is prepared as in Example 8, but with isopropanol.

White, amorphous powder.

Rf: 0.35 (silica gel; ethyl acetate/methanol/triethylamine 85/10/5)

$C_{31}H_{36}Cl_2N_6O_8$ (M: 691.6)

| $^1$H—NMR data: (d$_6$-DMSO, TMS as internal standard) | δ = 1.43 (d) 6 H, 3.2 (m) 4 H, 3.8 (m) 8 H, 4.4 (m) 1 H, 4.9 (m) 2 H, 5.1 (m) 1 H, 6.70 (s) 2 H, 7.03 (m) 4 H, 7.3–8.3 (m) 6 H, of which 3 H exchangeable with D$_2$O, 7.90 (s) 1 H, 8.48 (s) 1 H ppm. |
|---|---|

EXAMPLE 10

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(2-methoxyethyl)-ester fumarate

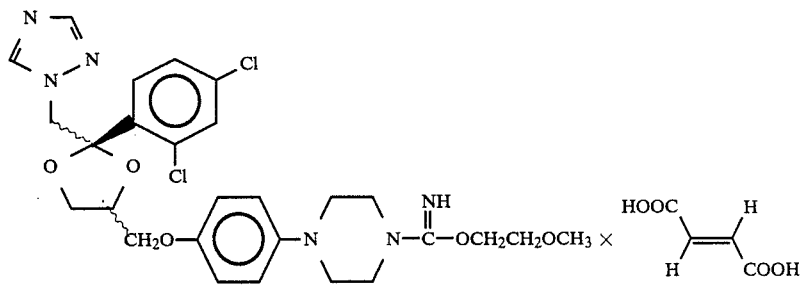

This compound is prepared as in Example 8, but with 2-methoxyethanol.

White, amorphous powder.

Rf: 0.27 (silica gel; ethyl acetate/methanol/triethylamine 85/10/5)

$C_{31}H_{36}Cl_2N_6O_9$ (M: 707.6)

| $^1$H—NMR data: (d$_6$-DMSO, TMS as internal standard) | δ = 3.12 (m) 4 H, 3.33 (s) 3 H, 3.4–4.15 (m) 10 H, 4.42 (m) 3 H, 4.85 (broad s) 2 H, 6.60 (s) 2 H, 6.7–7.35 (m) 7 H, 3 H exchangeable with D$_2$O, 7.4–7.7 (m), 7.92 (s) 1 H, 8.48 (s) 1 H ppm. |
|---|---|

EXAMPLE 11

(±)-cis-4-[4-[[2-(2,4-dichlorophenyl)-2-(imidazol-1-ylmethyl)-1,3-dioxolan-4-yl]-methoxy]-phenyl]-piperazine-1-carbimic acid-methylester

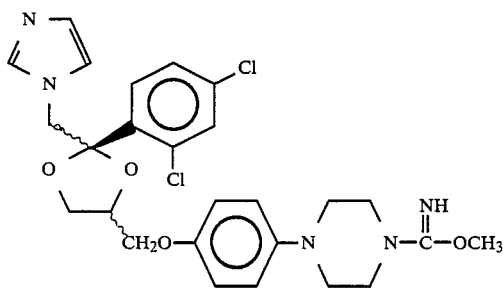

This compound is prepared as in Example 1, but with (±)-cis-1-cyano-4-[4-[[2-(2,4-dichlorophenyl)-2-imidazol-1-ylmethyl)-1,3-dioxolan-4-yl]-methoxy]-phenyl]-piperazine and methanol.

Colorless powder melting at 132.5°–134.5° C.

Rf: 0.22 (silica gel; ethyl acetate/methanol/triethylamine 85/10/5)

$C_{26}H_{29}Cl_2N_5O_4$ (M: 546.5)

| $^1$H—NMR data: (CDCl$_3$, TMS as internal standard) | $\delta$ = 3.1 (m) 4 H, 3.2–4.0 (m) 3 H, 1 H exchangeable with D$_2$O, 3.77 (s) 3 H, 4.37 (m) 1 H, 4.47 (m) 2 H, 6.87 (m) 4 H, 7.01 (m) 2 H, 7.2–7.7 (m) 4 H ppm. |
|---|---|

Preparation of (±)-cis-1-cyano-4-[4-[[2-(2,4-dichlorophenyl)-2-(imidazol-1-ylmethyl)-1,3-dioxolan-4-yl]-methoxy]-phenyl]-piperazine

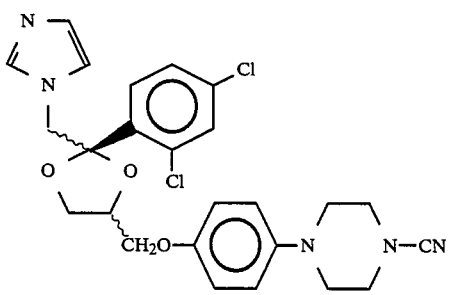

A solution of 4.07 g (20 mmoles) 1-cyano-4-(4-hydroxyphenyl)-piperazine in 20 ml DMF is added dropwise to a suspension of 675 mg (22.5 mmoles) sodium hydride (80% suspension in mineral oil) in 25 ml DMF. After the evolution of gas has stopped, 8.15 g (20 mmoles) (±)-cis-[2-(2,4-dichlorophenyl)-2-(imidazol-1-ylmethyl)-1,3-dioxolan-4-yl]-methyl-4-toluene sulfonate are added, followed by heating for 10 h at 90° C. The reaction mixture is then poured onto water, extracted with 1,2-dichloroethane and the organic phase washed with water. Removal of the solvent by distillation in vacuo leaves an oil which is purified by filtration over silica gel (eluent: ethyl acetate/ethanol 90/10). The title compound may be crystallized in the cold from a little methanol.

Yield: 5.3 g (52% of the theoretical)

Colorless powder melting at 118°–120° C.

Rf: 0.60 (silica gel; dichloromethane/methanol 90/10)

$C_{25}H_{25}Cl_2N_5O_3$ (M: 514.4)

| $^1$H—NMR data: (CDCl$_3$, TMS as internal standard) | $\delta$ = 3.13 (m) 4 H, 3.39 (m) 4 H, 3.55–4.1 (m) 4 H, 4.36 (m) 1 H, 4.46 (m) 2 H, 6.86 (m) 4 H, 7.02 (m) 2 H, 7.2–7.8 (m) 4 H ppm. |
|---|---|

EXAMPLE 12

(±)-cis-4-[4-[[2-(4-fluorophenyl)-2-(1H-1,2,4-triazol-1-ylmethyl)-1,3-dioxolan-4-yl]-methoxy]-phenyl]-piperazine-1-carbimic acid-methylester

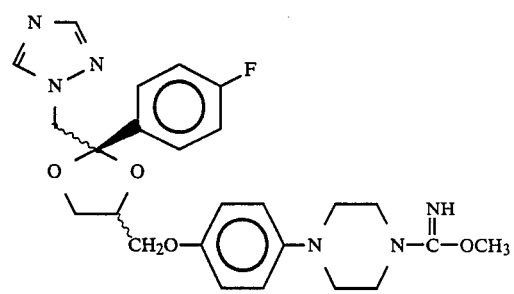

This compound is prepared as in Example 1, but with (±)-cis-1-cyano-4-[4-[[2-(4-fluorophenyl)-2-(1H-1,2,4-triazol-1-ylmethyl)-1,3-dioxolan-4-yl]-methoxy]-phenyl]-piperazine and methanol.

Colorless solid melting at 164°–166° C.

Rf: 0.40 (silica gel; dichloromethanol/methanol/NH$_3$ (25%) 90/9/1)

$C_{25}H_{29}FN_4O_4$ (M: 468.5)

| $^1$H—NMR data: (CDCl$_3$, TMS as internal standard) | $\delta$ = 3.07 (m) 4 H, 3.52 (m) 5 H, 3.77 (s) 3 H, 3.83 (m) 3 H, 4.2–4.9 (broad) 1 H, exchangeable with D$_2$O, 4.36 (m) 1 H, 4.53 (s) 2 H, 6.84 (m) 4 H, 7.10 (m) 2 H, 7.54 (m) 2 H, 7.94 (s) 1 H, 8.24 (s) 1 H ppm. |
|---|---|

Preparation of
(±)-cis-1-cyano-4-[4-[[2-(4-fluorophenyl)-2-(1H-1,2,4-triazol-1-ylmethyl)-1,3-dioxolan-4-yl]-methoxy]-phenyl]-piperazine

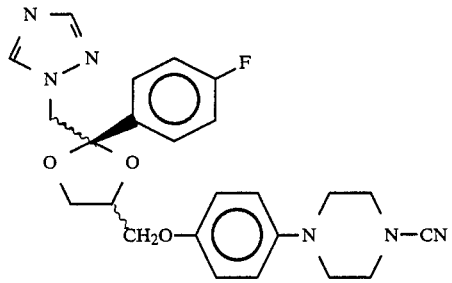

A solution of 3.66 g (18 mmoles) 1-cyano-4-(4-hydroxyphenyl)-piperazine in 40 ml DMF is added dropwise to a slurry of 0.66 g (22 mmoles) sodium hydride (80% dispersion in mineral oil) in 60 ml DMF. After the evolution of gas has stopped, 6.0 g (15 mmoles) (±)-cis-[2-(4-fluorophenyl)-2-(1H-1,2,4-triazol-1-ylmethyl)-1,3-dioxolan-4-yl]-methyl methane sulfonate are added, followed by heating for 5 h at 90° C. After cooling, the reaction mixture is poured onto 300 ml ice water. The title compound crystallizes in the form of a beige-colored solid which is recrystallized from a little ethyl acetate.

Yield: 4.9 g (70% of the theoretical)
Colorless powder melting at 152°–153° C.
Rf: 0.50 (silica gel; ethyl acetate/methanol 90/10)
$C_{24}H_{25}F_4N_6O_3$ (M: 464.5)

| | |
|---|---|
| $^1$H—NMR data: (CDCl$_3$, TMS as internal standard) | δ = 3.12 (m) 4 H, 3.39 (m) 5 H, 3.83 (m) 3 H, 4.35 (m) 1 H, 4.53 (s) 2 H, 6.86 (m) 4 H, 7.09 (m) 2 H, 7.53 (s) 2 H, 7.93 (s) 1 H, 8.25 (s) 1 H ppm. |

EXAMPLE 13

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-phenylester

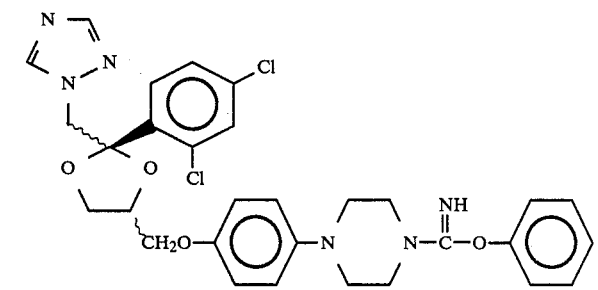

1.47 g (3 mmoles) (±)-cis-1-[4-[[2-(2,4-dichlorophenyl)-2-(1H-1,2,4-triazol-1-ylmethyl)-1,3-dioxolan-4-yl]-methoxy]-phenyl]-piperazine in 10 ml THF are added dropwise with stirring at room temperature to a solution of 0.39 g (3.3 mmoles) phenylcyanate. The reaction mixture undergoes an increase in temperature to 30° C. After stirring for 1 hour, the reaction mixture is concentrated in vacuo and the oily residue is taken up in 30 ml ethyl acetate. The title compound crystallizes in the form of a colorless solid by stirring the solution in an ice bath.

Yield: 1.50 g (82% of the theoretical)
Colorless crystals melting at 152.5°–153° C.
Rf: 0.50 (silica gel; ethyl acetate/methanol/triethylamine 90/5/5)
$C_{30}H_{30}Cl_2N_6O_4$ (M: 609.5)

| | |
|---|---|
| $^1$H—NMR data: (CDCl$_3$, TMS as internal standard) | δ = 3.17 (m) 4 H, 3.4–4.15 (m) 8 H, 4.38 (m) 2 H, 1 H exchangeable with D$_2$O, 4.83 (s) 2 H, 6.7–7.8 (m) 12 H, 7.95 (s) 1 H, 8.27 (s) 1 H ppm. |

EXAMPLE 14

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(3-methylphenyl)-ester

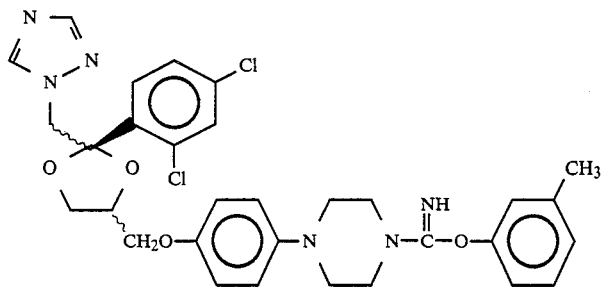

This compound is prepared as in Example 13, but with 3-methylphenylcyanate.
Yield: 1.28 g (68% of the theoretical).
Pale yellowish crystals melting at 163°–165° C.
Rf: 0.46 (silica gel; ethyl acetate/methanol/triethylamine 90/5/5)
$C_{31}H_{32}Cl_2N_6O_4$ (M: 623.5)

| $^1$H—NMR data: (CDCl$_3$, TMS as internal standard) | δ = 2.37 (s) 3 H, 3.13 (m) 4 H, 3.4–4.1 (m) 8 H, 4.33 (m) 2 H, 1 H exchangeable with D$_2$O, 4.81 (s) 2 H, 6.7–7.8 11 H, 7.93 (s) 1 H, 8.25 (s) 1 H ppm. |
|---|---|

EXAMPLE 15

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(4-methoxyphenyl)-ester

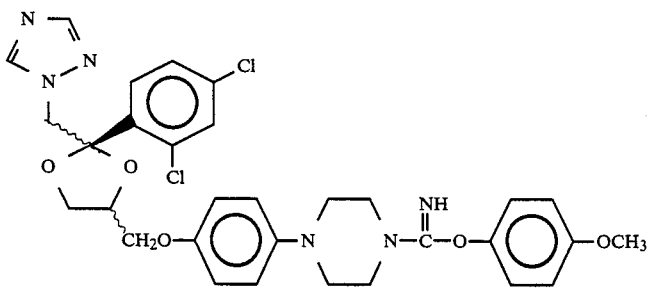

This compound is prepared as in Example 13, but with 4-methoxyphenylcyanate.
Colorless crystals melting at 176.5°–177.5° C.
Rf: 0.47 (silica gel; ethyl acetate/methanol/triethylamine 85/10/5)
$C_{31}H_{32}Cl_2N_6O_5$ (M: 639.5)

| $^1$H—NMR data: (CDCl$_3$, TMS as internal standard) | δ = 2.37 (s) 3 H, 3.4–4.1 (m) 9 H, exchangeable with D$_2$O, 3.83 (s) 3 H, 4.38 (m) 1 H, 4.82 (s) 2 H, 6.90 (m) 4 H, 7.01 (m) 4 H, 7.2–7.7 (m) 3 H, 7.93 (s) 1 H, 8.25 (s) 1 H ppm. |
|---|---|

EXAMPLE 16

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(2,2,2-trifluoroethyl)-ester

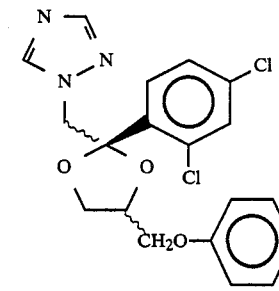

This compound is prepared as in Example 13, but with 2,2,2-trifluoroethylcyanate Colorless crystals melting at 134.5°–135° C. (ethyl acetate/diethyl ether)
Rf: 0.52 (silica gel; ethyl acetate/methanol/triethylamine 90/5/5)
$C_{26}H_{27}F_3Cl_2N_6O_4$ (M: 615.4)
Calculated: C, 50.74; H, 4.42; N, 13.66; Found: C, 50.82; H, 4.52; N, 13.90.

| $^1$H—NMR data: (CDCl$_3$, TMS as internal standard) | δ = 3.1 (m) 4 H, 3.5 (m) 5 H, 3.85 (m) 3 H, 4.4 (m) 1 H, |
|---|---|

-continued

| | |
|---|---|
| | 4.60 (q) 2 H, |
| | 4.83 (s) 2 H, |
| | 4.2–5.5 (broad) 1 H, exchangeable with D$_2$O, |
| | 6.90 (m) 4 H, |
| | 7.2–7.8 (m) 3 H, |
| | 7.95 (s) 1 H, |
| | 8.27 (s) 1 H ppm. |

EXAMPLE 17

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-carbimic acid-(4-chlorophenyl)-ester

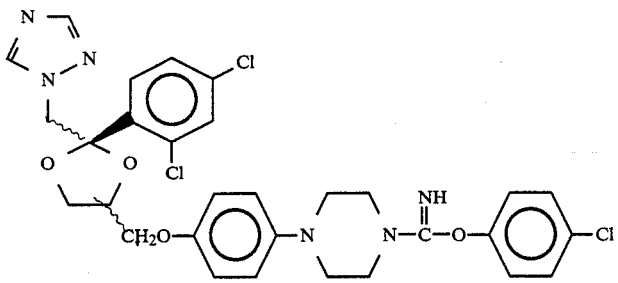

This compound is prepared as in Example 13, but with 4-chlorophenylcyanate.

Colorless crystals melting at 161°–163° C.
Rf: 0.54 (silica gel; ethyl acetate/methanol/triethylamine 90/5/5)
C$_{30}$H$_{29}$Cl$_3$N$_6$O$_4$ (M: 644.0)

| $^1$H—NMR data: (CDCl$_3$, TMS as internal standard) | $\delta$ = 3.14 (m) 4 H, 3.4–4.15 (m) 8 H, 4.40 (m) 1 H, 4.7–5.3 (broad) 1 H, exchangeable with D$_2$O, 4.84 (s) 2 H, 6.7–7.8 (m) 11 H, 7.95 (s) 1 H, 8.27 (s) 1 H ppm. |
|---|---|

EXAMPLE 18

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-thiocarbimic acid-methylester

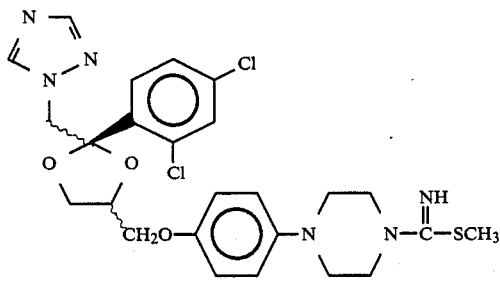

10.0 g (20.4 mmoles) (±)-cis-4-[4-[[2-(2,4-dichlorophenyl)-2-(1H-1,2,4-triazol-1-ylmethyl)-1,3-dioxolan-4-yl]-methoxy]-phenyl]-piperazine are slurried in 100 ml acetonitrile, followed by the addition of 5.08 g (20.4 mmoles) iminodithiocarbonic acid dimethylester hydriodide. The reaction mixture is heated for 2 h to the reflux temperature, cooled and poured onto 200 ml of a 10% aqueous potassium carbonate solution. Extraction with ethyl acetate gives 15.0 g of a semi-crystalline mass which is chromatographed on silica gel (eluent: ethyl acetate/methanol/triethylamine 90/5/5). The title compound is then recrystallized from tert.-butyl methyl ether.

Yield: 4.95 g (43% of the theoretical)
Colorless crystals melting at 160°–161° C.
Rf: 0.43 (silica gel; ethyl acetate/methanol/triethylamine 90/5/5)
C$_{25}$H$_{28}$Cl$_2$N$_6$O$_3$S (M: 563.5)

| $^1$H—NMR data: (CDCl$_3$, TMS as internal standard) | $\delta$ = 2.32 (s) 3 H, 3.08 (m) 4 H, 3.4–4.15 (m) 8 H, 4.37 (m) 1 H, 4.81 (m) 2 H, 5.8–6.3 (broad), 1 H, exchangeable with D$_2$O, 6.88 (m) 4 H, 7.15–7.8 (m) 3 H, 7.83 (s) 1 H, 8.28 (s) 1 H ppm. |
|---|---|

EXAMPLE 19

(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-(N-methyl)-thiocarbimic acid-methylester

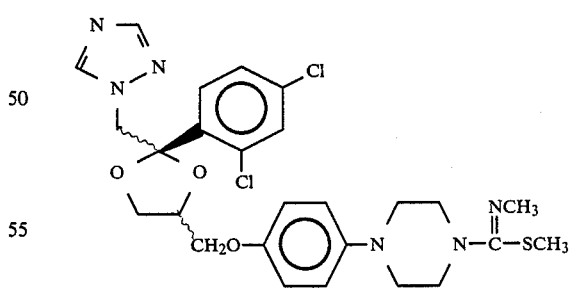

7 g (12.5 mmoles) (±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-(N-methyl)-carbothiamide are dissolved in 200 ml 1,2-dichloroethane, followed by the dropwise addition of 2.7 g (18.6 mmoles) methyliodide. After heating for 4 h at 40° C., the reaction mixture is washed with a total of 200 ml 10% aqueous potassium carbonate solution and the solvent is removed in vacuo. The residue is crystallized from tert.-butyl methyl ether.

Yield: 6.9 g (96% of the theoretical)
Yellowish colored powder melting at 71°–73° C.
Rf: 0.50 (silica gel; ethyl acetate/methanol/triethylamine 90/5/5)
$C_{26}H_{30}Cl_2N_6O_3S$ (M 577.5)

| $^1$H—NMR data: (CDCl$_3$, TMS as internal standard) | $\delta$ = 2.29 (s) 3 H, 3.09 (m) 4 H, 3.19 (s) 3 H, 3.40 (m) 5 H, 3.80 (m) 3 H, 4.33 (m) 1 H, 4.73 (s) 2 H, 6.83 (m) 4 H, 7.1–7.7 (m) 3 H, 7.88 1 H, 8.21 1 H ppm. |
|---|---|

Preparation of
(±)-cis-4-[4-[[2-(2,4-dichlorophenyl)-2-(1H-1,2,4-triazol-1-ylmethyl)-1,3-dioxolan-4-yl]-methoxy]-phenyl]-piperazine-1-(N-methyl)-carbothiamide

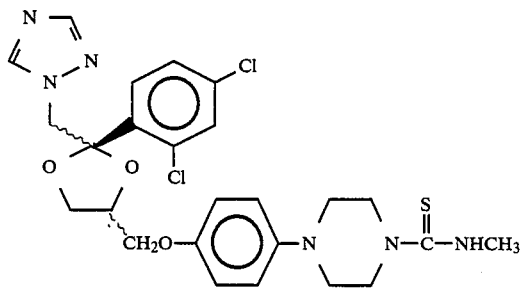

1.5 g (20 mmoles) methylisothiocyanate are added at room temperature to 9.8 g (20 mmoles) (±)-cis-1-[4-[[2-(2,4-dichlorophenyl)-2-(1H-1,2,4-triazol-1-ylmethyl)-1,3-dioxolan-4-yl]-methoxy]-phenyl]-piperazine in 50 ml dichloromethane. After 1 h, the reaction mixture is concentrated in vacuo and the residue recrystallized from ethyl acetate.

Yield: 9.5 g (85% of theoretical)
Colorless solid melting at 151°–152° C.
Rf: 0.55 (silica gel; ethyl acetate/methanol 80/20)
$C_{25}H_{28}Cl_2N_6O_3S$ (M: 563.51)

| $^1$H—NMR data: (CDCl$_3$, TMS as internal standard) | $\delta$ = 3.17 (m) 7 H, 3.4–4.2 (m) 8 H, 4.39 (m) 1 H, 4.83 (s) 2 H, 6.0 1 H, exchangeable with D$_2$O, 6.88 (m) 4 H, 7.2–7.7 (m) 3 H, 7.94 (s) 1 H, 8.27 (s) 1 H ppm. |
|---|---|

We claim:
1. 1,4-piperazine compounds corresponding to the following formula

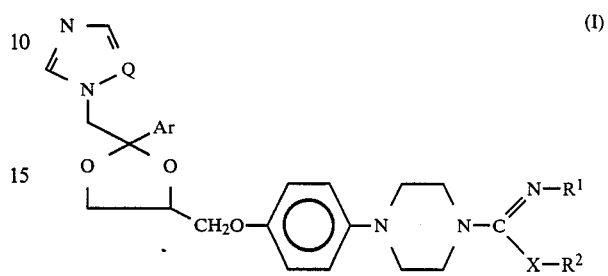

in which
Q represents CH or N,
Ar is an unsubstituted phenyl group or a phenyl group substituted by up to 2 halogen atoms,
X is an oxygen or sulfur atom,
$R^1$ if a hydrogen atom or a lower alkyl radical and $R^2$ is a $C_1$–$C_{10}$ alkyl, $C_5$–$C_{12}$ cycloalkyl, $C_1$–$C_{10}$ alkenyl, halogen-$C_1$–$C_{10}$-alkyl, hydroxy-$C_1$–$C_{10}$-alkyl, $C_1$–$C_{10}$-alkoxy-$C_1$–$C_{10}$-alkyl, di-$C_1$–$C_{10}$-alkylamino-$C_1$–$C_{10}$ alkyl, Ar lower alkyl or aryl radical which is either unsubstituted or substituted by 1 to 3 substituents selected from fluorine, chlorine and bromine atoms, $C_1$–$C_3$-alkyl and $C_1$–$C_3$-alkoxy and physiologically acceptable hydrates and salts thereof.

2. 1,4-piperazine compounds as claimed in claim 1, characterized in that X is an oxygen atom and $R^1$ is a hydrogen atom, and physiologically acceptable hydrates and salts thereof.

3. (±)-cis-4-[4-[[2-(2,4-dichlorophenyl-2-(1H-1,2,4-triazol-1-yl-methyl)-1,3-dioxolan-4-yl]-methoxy]-phenyl]-piperazine-1-carbimic acid-(2,2,2-trifluoroethyl)-ester and physiologically acceptable acid addition salts thereof.

4. (±)-cis-4-[4-[[2-(2,4-dichlorophenyl)-1-(1H-1,2,4-triazol-1-yl-methyl)-1,3-dioxolan-4-yl]-methoxy]-phenyl]-piperazine-1-carbimic acid methyl ester and physiologically acceptable acid addition salts thereof.

5. (±)-cis-4-[4-[[2-(2,4-dichlorophenyl)-2-(1H-1,2,4-triazol-1-yl-methyl)-1,3-dioxolan-4-yl]-methoxy]-phenyl]-piperazine-1-carbimic acid-(4-methoxyphenyl)-ester and physiologically acceptable acid addition salts thereof.

6. An antimycotic pharmaceutical composition comprising a compound of the type claimed in claims 1, 2, 3, 4 or 5 and at least one inert, pharmaceutically acceptable excipient or an inert, pharmaceutically acceptable diluent.

* * * * *